United States Patent [19]

Babler

[11] 4,175,204

[45] Nov. 20, 1979

[54] METHOD OF PREPARING E-4-ACETOXY-2-METHYL-2-BUTENAL

[76] Inventor: James H. Babler, 125 Callan, Evanston, Ill. 60202

[21] Appl. No.: 1,075

[22] Filed: Jan. 8, 1979

Related U.S. Application Data

[63] Continuation-in-part of Ser. No. 871,075, Jan. 20, 1978, abandoned.

[51] Int. Cl.$^2$ .............................................. C07C 67/28
[52] U.S. Cl. ................................ 560/262; 260/601 R; 560/238; 560/240; 560/241
[58] Field of Search ............................. 560/262, 241; 260/601 R, 602

[56] References Cited

U.S. PATENT DOCUMENTS

| | | | |
|---|---|---|---|
| 2,511,870 | 6/1950 | Oroshnik | 560/262 |
| 3,213,155 | 10/1955 | Schriesheim et al. | 562/545 |
| 4,048,220 | 9/1977 | Cardenas | 560/237 |

FOREIGN PATENT DOCUMENTS 736488  9/1955  United Kingdom ..................... 560/262

OTHER PUBLICATIONS

Babler et al., Tetrahedron Letters, 239 (1976).
Ganem, Tetrahedron Letters, 917–920 (1974).

*Primary Examiner*—Vivian Garner
*Attorney, Agent, or Firm*—Merriam, Marshall & Bicknell

[57] ABSTRACT

E-4-acetoxy-2-methyl-2-butenal is prepared by: (1) preparation of an intermediate allylic halide from isoprene; and (2) reaction of the allylic halide with dimethyl sulfoxide in the presence of a non-nucleophilic base to form the desired product.

10 Claims, No Drawings

METHOD OF PREPARING E-4-ACETOXY-2-METHYL-2-BUTENAL

BACKGROUND OF THE INVENTION

This application is a continuation-in-part of applicant's co-pending application—Ser. No. 871,075, filed Jan. 20, 1978, now abandoned, entitled, "Method of Preparing E-4-acetoxy-2-methyl-2-butenal."

Reif et al. have described a commercial process for the production of Vitamin A acetate [*Chemie-Ing.-Techn.* 45, 646–652 (1973)]. The final step of the synthesis involves a reaction between a $C_{15}$ triphenylphosphonium salt and a $C_5$ acetate:

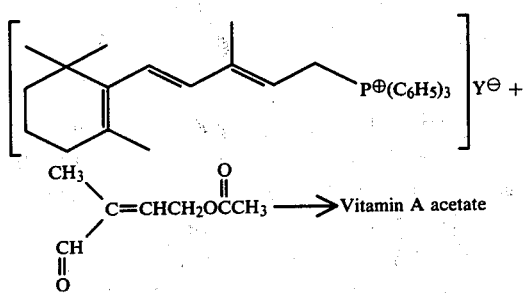

As a method for preparing the $C_5$ acetate (i.e., β-formylcrotyl acetate, systematically named E-4-acetoxy-2-methyl-2-butenal) for use in the above reaction, Reif et al. show a multi-step process involving an oxidation reaction:

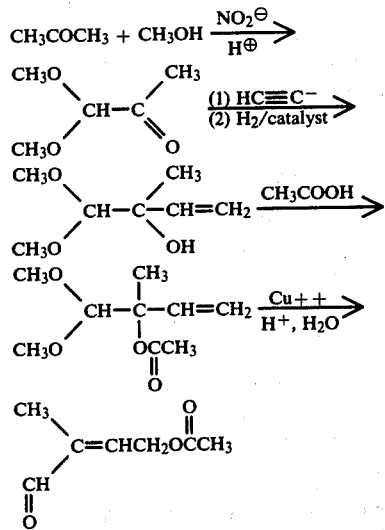

The Reif et al. synthesis is suggested in U.S. Pat. No. 3,478,060, and in the references cited therein.

Another process for synthesizing the $C_5$ acetate has been described in the recent literature by Wehrli et al. [*Synthesis*, 9, 649–50 (Sept. 1977)]. Wehrli's reaction involves a nitroacetoxylation of isoprene followed by a reduction of the resultant nitro acetate with iron in the presence of acetic acid. Overall yields of 40% of desired $C_5$ acetate are reported. The reaction involves the use of heat and a potentially hazardous compound, acetyl nitrate.

BRIEF SUMMARY

The present invention relates to an improved process for producing E-4-acetoxy-2-methyl-2-butenal, a $C_5$ acetate which can be used in Vitamin A synthesis. In one embodiment, practice of the method of the invention utilizes easily available isoprene and acetic acid as starting materials, proceeds at room temperature, requires only two reaction steps, and yields substantially quantitative amounts of the desired $C_5$ acetate according to the following reaction scheme:

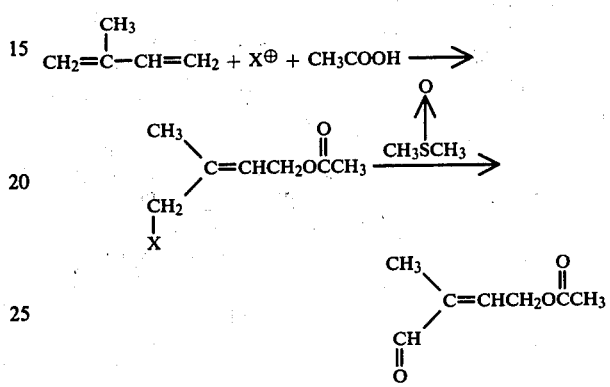

Preparation of 4-halo-3-methyl-2-buten-1-ol acetate (a) The direct method

An initial step in applicant's process of synthesizing E-4-acetoxy-2-methyl-2-butenal involves the preparation of a 4-halo-3-methyl-2-buten-1-ol acetate intermediate. This intermediate may be prepared directly, in a one-step reaction by the addition of a source of positive halogen, X+, to a solution of isoprene in acetic acid according to a process described by applicant and his co-worker [J. Babler and W. Buttner, *Tetrahedron Lett.*, 239 (1976)]. Compounds providing suitable sources of positive halogen for this reaction include acid solutions of N-bromosuccinimide or a hypochlorite such as tert-butyl hypochlorite, as illustrated in the following reactions.

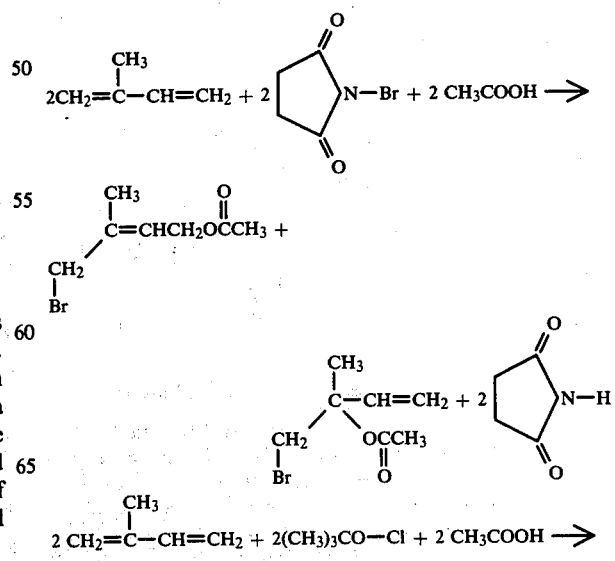

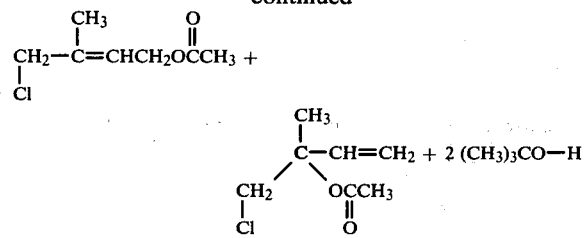

The first reaction yields approximately 75% by weight of the allylic halide as the desired 1,4 adduct and 25% as a 1,2 adduct. Both the 1,4 adduct (systematically named 4-bromo-3-methyl-2-buten-1-ol acetate) and the 1,2 adduct (1-bromo-2-acetoxy-2-methyl-3-butene) are readily separable both from the reaction mixture and from one another by fractional distillation.

Yield of the desired 1,4 adduct can be further enhanced. The isolated 1,2 adduct, in the presence of a strong acid catalyst, will be quantitatively isomerized to the desired 4-bromo-3-methyl-2-buten-1-ol acetate. A similar isomerization was reported by W. Oroshnik and R. A. Mallory [*J. Amer. Chem. Soc.*, 72, 4608 (1950)].

(b) The two-step reaction

Another method of synthesizing the 4-halo-3-methyl-2-buten-1-ol acetate which should offer economic advantages over the foregoing direct reactions, utilizes two reaction steps. The first step involves the synthesis of 1-chloro-2-methyl-3-buten-2-ol, which may be synthesized from isoprene in accordance with a process suggested in British Patent 978,892 to Dunlop Rubber Company:

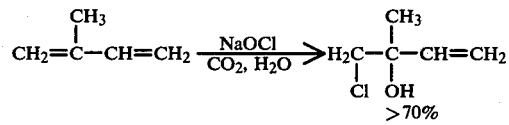

Another route to this intermediate is suggested elsewhere in the literature [*Chem. Abstracts*, 80, 59,36ly (1974)].

This resultant 1-chloro-2-methyl-3-buten-2-ol may be rearranged to the desired 4-chloro-3-methyl-2-buten-1-ol acetate intermediate by means of an isomerization reaction such as that suggested by applicant in U.S. Pat. No. 3,927,076.

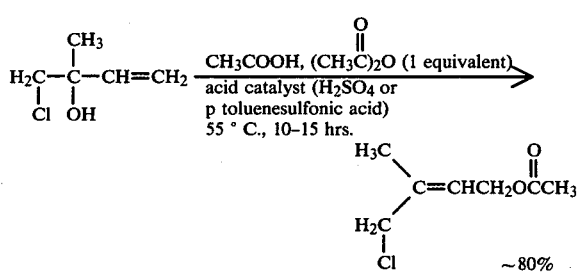

Preparation of E-4-acetoxy-2-methyl-2-butenal

The optimum route to the desired product, E-4-acetoxy-2-methyl-2-butenal, depends on which primary halide intermediate is used. Thus, when the primary bromide, 4-bromo-3-methyl-2-buten-1-ol acetate, is employed, the product may be obtained directly by the addition of dimethyl sulfoxide (DMSO) in the presence of a non-nucleophilic base such as sodium bicarbonate. The oxidation reaction proceeds at room temperature with yields of aldehyde in excess of 80%.

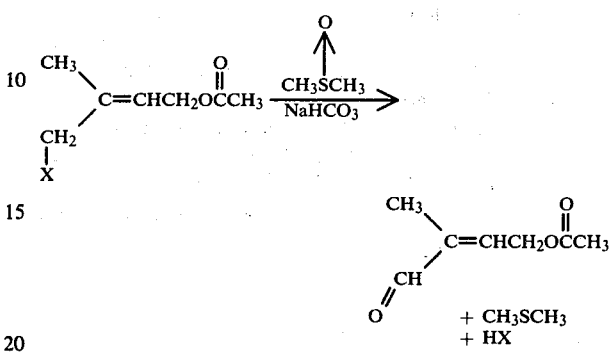

In the case of the primary allylic chloride, although DMSO and a bicarbonate base can be used to oxidize the allylic chloride, the reaction does not proceed at room temperature nor does it provide as quantitative a result as that involving the primary bromide. The yield of desired $C_5$ acetate is moderate ($\sim$ 40–50%) and unidentified by-products are formed which are not present in significant amounts when 4-bromo-3-methyl-2-buten-1-ol acetate is oxidized with DMSO in the presence of the bicarbonate.

However, the DMSO oxidation of the primary allylic chloride to the desired β-formylcrotyl acetate will be successful when a different non-nucleophilic base is utilized in the reaction—a dibasic metal phosphate such as $Na_2HPO_4$ or $K_2HPO_4$:

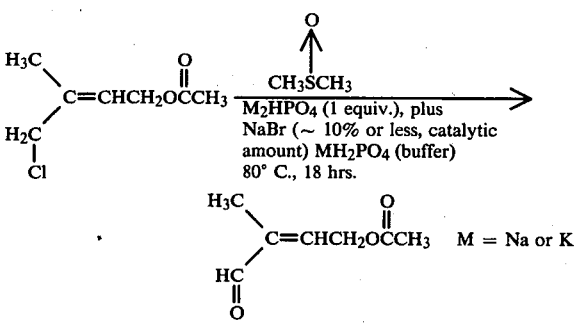

Use of a bromide salt such as sodium bromide and a monobasic metal phosphate buffer is desirable, but not necessary.

Although the oxidation of a primary alkyl halide by dimethyl sulfoxide to form an aldehyde is a known reaction, applicant has found no report in the literature of the successful use of dimethylsulfoxide under "SN2-type" conditions for oxidation of an allylic halide. This gap in the literature is no doubt attributable to the expectation that DMSO treatment of allylic halides would generate an elimination reaction (I→II)

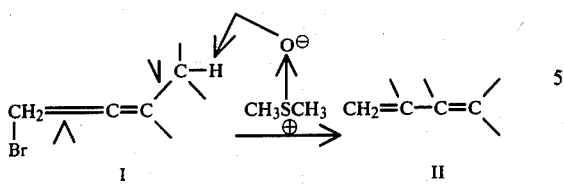
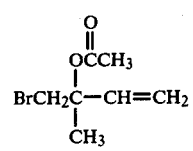

rather than follow an oxidation route, as is required to form an aldehyde.

Indeed, applicant has found that when numerous primary allylic bromides are reacted under the same conditions utilized according to the invention to form the desired C5 acetate, the products consist almost exclusively of elimination products of general structure II. Primary allylic bromides tested in this manner include 1-bromo-2-octadecene, 1-bromo-3-propyl-2-hexene, and 1-bromo-3, 7-dimethyl-2,6-octadiene (geranyl bromide). The result, in each case, was the formation of a conjugated 1,3diolefinic structure rather than the formation of the aldehyde.

Similar results are disclosed in a journal article by Ganem et al., *Tetrahedron Lett.*, 917–20 (1974), where it is reported that the reaction of a primary allylic halide such as 1,4-dibromo-trans-2,3-dimethyl-2-butene with DMSO in the presence of a non-nucleophilic base fails to yield any dialdehyde under applicant's reaction conditions. These authors suggest that preparation of the aldehyde from primary allylic halides requires the use of a non-nucleophilic silver salt such as silver tetrafluoroborate, the initial step proceeding via a "SN1" reaction rather than an "SN2" reaction like applicant's.

DETAILED DESCRIPTION

The following examples illustrate in greater detail practice of the present invention and more specifically, (i) the formation of a desired 4-halo intermediate, 4-bromo-3-methyl-2-butene-1-ol acetate; (ii) the isomerization of a 1,2 adduct to the 1,4 adduct, 4-bromo-3-methyl-2-butene-1-ol acetate; (iii) the formation of another 4-halo intermediate, 4-chloro-3-methyl-2-butene-1-ol acetate; (iv) preparation of the desired C5 acetate, E-4-acetoxy-2-methyl-2-butenal from a primary allylic bromide; and (v) preparation of the desired C5 acetate from a primary allylic chloride.

EXAMPLE I 4-bromo-3-methyl-2-buten-1-ol acetate 93.6 g (526 mmoles) of N-bromosuccinimide (NBS) was added in portions over a period of 60 minutes to a well-stirred solution of 75 ml (0.73 mole) of isoprene in 300 ml of glacial acetic acid. After stirring this mixture at room temperature for an additional 30 minutes, it was diluted with 1,500 ml of water and the product was isolated by extraction with dichloromethane. The extracts were washed with saturated sodium bicarbonate solution, 10% sodium chloride solution, dried over anhydrous magnesium sulfate, and filtered. Removal of the dichloromethane by evaporation at reduced pressure yielded 108 g (99%) of crude product, which was subsequently separated into two components by fractional distillation:

Fraction 1: bp 65° at 3.0 mm; approximately 25 g (23%) was collected and shown to be the 1,2-adduct:

Fraction 2: bp 57°–65° (0.20 mm); 60.1 g (55%) of material was collected and shown to be the 1,4-adduct (as a 70:30 mixture of E:Z stereoisomers):

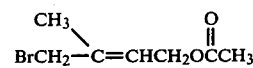

4-bromo-3-methyl-2-buten-1-ol acetate

In a larger-industrial-scale process, an alternative procedure could be used. After dilution of the mixture with water, the desired 1,2- and 1,4-adducts can be removed from the reaction mixture by continuous extraction with heptane or hexane. The acetic acid, in turn, can be removed from the remaining aqueous layer by continuous extraction with benzene, ether, or chloroform. The resultant aqueous layer will contain succinimide. If one equivalent of sodium hydroxide is added to the aqueous solution and the solution cooled to 0° C., addition of one equivalent of bromine will produce N-bromosuccinimide which quickly precipitates out of the aqueous medium and which may be recycled in the reaction.

EXAMPLE II 4-bromo-3-methyl-2-buten-1-ol acetate from 1-bromo-2-acetoxy-2-methyl-3-butene A solution of 275 mg of 1,2 adduct in 6 ml of glacial acetic acid containing 1 ml of acetic anhydride and 100 mg of p-toluenesulfonic acid was allowed to stand at room temperature for 90 hours. The mixture was then diluted with 50 ml of water and the product was isolated by extraction with dichloromethane. The extracts were washed thoroughly with 1M aqueous NaOH, 10% aqueous sodium chloride, dried over anhydrous magnesium sulfate, and filtered. Removal of the dichloromethane by evaporation at reduced pressure afforded 159 mg (58%) of a product having IR and NMR spectra virtually identical to those of a pure sample of the 1,4 adduct.

Other strong acid catalysts ($K_a \geqq 10^{-2}$) such as sulfuric acid can be used to effect this transformation.

EXAMPLE III 4-chloro-3-methyl-2-buten-1-ol acetate, via 1-chloro-2-methyl-3-buten-2-ol Isoprene (4 moles) was added to bleaching powder (NaOCl, 0.85 mole) in 3500 ml of $H_2O$ at 0°. The mixture was stirred and $CO_2$ was passed into it for 4 hours. The product, 1-chloro-2-methyl-3-buten-2-ol, was isolated by continuous extraction with dichloromethane and was purified by simple distillation: bp 41°–2° C. at 11 mm.

A mixture of 240 mg. (1.26 mmoles) of p-toluene-sulfonic acid monohydrate in 1.0 ml of acetic anhydride and 5.0 ml of glacial acetic acid was added dropwise (with external cooling of the reaction mixture in a cold water bath) to a solution of 1.67 g. (13.86 mmoles) of 1-chloro-2-methyl-3-buten-2-ol and 1.0 ml of acetic anhydride in 6.0 ml of glacial acetic acid. This mixture was then heated at 55° C. (bath temperature) for 15 hours. The product was isolated by pouring the mixture into ice-cold aqueous sodium hydroxide (enough to neutralize the acetic acid) and extracting with ether. (The product can also be isolated by diluting the mixture with 10 volumes of iced water and continuous extraction with cyclohexane.) The yield of 1° allylic acetate (containing no 3° acetate) was 1.94 g. (11.94 mmoles, 86% yield).

EXAMPLE IV

E-4-acetoxy-2-methyl-2-butenal from 4-bromo-3-methyl-2-buten-1-ol acetate

A mixture of 1.10 g (5.3 mmoles) of 4-bromo-3-methyl-2-buten-1-ol acetate prepared according to Example I and 500 mg (5.95 mmoles) of sodium bicarbonate in 8 ml of anhydrous dimethyl sulfoxide was stirred vigorously at room temperature for approximately 20 hours. The product was isolated by diluting the mixture with 50 ml of $H_2O$ and extracting thoroughly with dichloromethane. The combined extracts were washed with 10% sodium chloride solution, dried over anhydrous magnesium sulfate, and filtered. Removal of the dichloromethane by evaporation at reduced pressure, followed by chromatography on silica gel (elution with hexane—15% ether), afforded 0.61 g (81% yield) of the desired aldehyde. When a non-nucleophilic base ($NaHCO_3$) was omitted from the reaction mixture, the oxidation reaction was not observed.

EXAMPLE V

E-4-acetoxy-2-methyl-2-butenal from 4-chloro-3-methyl-2-buten-1-ol acetate

To a 25 ml flask equipped with an efficient stirrer and Vigreux column connected to a small distillation head were added 536 mg (3.3 mmole) of 4-chloro-3-methyl-2-buten-1-ol acetate, 4 ml of anhydrous dimethyl sulfoxide, 662 mg (3.80 mmole) of $K_2HPO_4$ (potassium phosphate, dibasic), 138 mg (1.02 mmole) of $KH_2PO_4$, and 40 mg (0.38 mmole) of sodium bromide. This mixture was then heated, protected from atmospheric moisture, at 80° C. (bath temperature) for 18 hours. The product was isolated by cooling the mixture to room temperature, pouring it into 40 ml of water, and extracting thoroughly with carbon tetrachloride. The yield of crude aldehyde was 452 mg (97% yield). GC analysis indicated the product was mainly a mixture of two components: >83% of this material was E-4-acetoxy-2-methyl-2-butenal (trans configuration for the double bond), and most of the rest was an unidentified, non-aldehydic compound (14% of the mixture). This latter impurity is the same one produced when the oxidation is effected on the allylic bromide at room temperature, in accordance with the procedure of Example IV. Since it has a considerably higher boiling point than the desired aldehyde, simple fractional distillation can be used to separate the two compounds. The yield of the desired aldehyde, β-formylcrotyl acetate, after purification on a small scale by column chromatograhy on silica gel, is 82%—comparable to that obtained in Example IV at room temperature. It was also observed that the aldehyde product formed under the above conditions at 80° C. contained none of the stereoisomeric Z-4-acetoxy-2-methyl-2-butenal shown below:

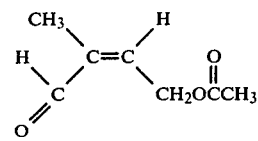

The above examples indicate that the desired $C_5$ acetate may be prepared by the general synthetic steps consisting of: (a) forming a first reaction mixture of isoprene, acetic acid, and a source of positive halogen; (b) isolating 4-halo-3-methyl-2-buten-1-ol acetate as a reaction product from said first reaction mixture; and (c) forming a second reaction mixture of 4-halo-3-methyl-2-buten-1-ol acetate and dimethyl sulfoxide; (d) isolating E-4-acetoxy-2-methyl-2-butenal as a reaction product from said second reaction mixture. More specifically, the particular steps employed in successful practice of the invention may involve the following in sequence:

(a) preparing in a vessel a room temperature solution of 1.4 parts of isoprene in ten parts of glacial acetic acid;

(b) adding one part of N-bromosuccinimide to said room temperature solution with constant stirring for a suitable time;

(c) adding to said vessel a quantity of water sufficient to increase the volume approximately five-fold whereby a dilute solution is formed;

(d) extracting said dilute solution with volumes of dichloromethane;

(e) washing said dichloromethane extracts with aqueous solutions of saturated sodium bicarbonate, 10% sodium chloride;

(f) drying said washed extracts with anhydrous magnesium sulfate and filtering said dried extracts;

(g) removing said dichloromethane from said filtered extracts by evaporation at reduced pressure whereby crude intermediate remains;

(h) fractionally distilling said crude intermediate at reduced pressure and elevated temperature;

(i) isolating the intermediate fraction having a boiling point at 0.20 mm of between 57° C. and 65° C.;

(j) adding said isolated intermediate fraction to a second reaction vessel containing a molar excess of anhydrous dimethyl sulfoxide and sodium bicarbonate;

(k) stirring said second reaction vessel at room temperature for 20 hours;

(l) adding a quantity of water sufficient to dilute the contents of said second vessel approximately six-fold;

(m) extracting the diluted contents of said second vessel with successive quantities of dichloromethane, washing and drying said extracts, and removing said dichloromethane by evaporation at reduced pressure; and (n) isolating the desired product by the use of chromatography.

Numerous modifications and variations in the practice of the invention are expected to occur to those skilled in the art upon consideration of the foregoing examples.

Although N-bromosuccinimide was employed as the source of positive halogen in Example I, it is known that hypohalites such as tert-butyl hypochlorite may also be employed. The source of positive halogen can be an N-halosuccinimide or a hypohalite. Similarly, suitable non-nucleophilic bases other than sodium bicarbonate [e.g., 2,4,6-trimethylpyridine (collidine)] may be employed in the synthesis illustrated in Example IV.

However, in the case of the primary chlorides, the DMSO oxidation proceeds much more favorably when a dibasic metal phosphate is used as the non-nucleophilic catalyst (Example V). As noted previously, all reactions may proceed at room temperature and under atmospheric pressure, although the formation and oxidation of primary chlorides is facilitated by use of moderate elevated temperatures (50° to 80°). It is expected, however, that obvious variations in these reaction conditions may be desirable for large scale production, and such alterations are within the contemplation of the invention.

The foregoing detailed description has been given for clearness of understanding only and no unnecessary limitations should be understood therefrom, as modifications will be obvious to those skilled in the art.

What is claimed is:

1. A process for synthesis of E-4-acetoxy-2-methyl-2-butenal comprising the following steps in sequence:
   (a) forming a reaction mixture of 4-halo-3-methyl-2-buten-1-ol acetate, dimethyl sulfoxide, and a non-nucleophilic base;
   (b) isolating E-4-acetoxy-2-methyl-2-butenal as a reaction product from said reaction mixture.

2. A process for synthesis of E-4-acetoxy-2-methyl-2-butenal comprising the following steps in sequence:
   (a) forming a first reaction mixture of isoprene, acetic acid and a source of positive halogen;
   (b) isolating 4-halo-3-methyl-2-buten-1-ol acetate as a reaction product from said first reaction mixture; and
   (c) forming a second reaction mixture of 4-halo-3-methyl-2-buten-1-ol acetate, dimethyl sulfoxide, and a non-nucleophilic base;
   (d) isolating E-4-acetoxy-2-methyl-2-butenal as a reaction product from said second reaction mixture.

3. The process of claim 2 wherein said source of positive halogen is a member selected from the group consisting of N-halosuccinimide or a hypohalite.

4. The process of claim 2 wherein said non-nucleophilic base is sodium bicarbonate.

5. The process of claim 2 wherein said source of positive halogen is N-bromosuccinimide and said reaction product isolated from said first reaction mixture is 4-bromo-3-methyl-2-buten-1-ol acetate.

6. The process of claim 5 further including the following steps in sequence:
   (a) isolating 1-bromo-2-acetoxy-2-methyl-3-butene as a reaction product from said first reaction mixture; and
   (b) forming a third reaction mixture of 1-bromo-2-acetoxy-2-methyl-3-butene, an acid catalyst, and acetic acid; and
   (c) isolating 4-bromo-3-methyl-2-buten-1-ol acetate as a reaction product from said third reaction mixture.

7. The process of claim 6 wherein said acid catalyst is selected from the group consisting of p-toluene-sulfonic acid, and sulfuric acid.

8. A process for synthesis of E-4-acetoxy-2-methyl-2-butenal comprising the following steps in sequence:
   (a) forming a first reaction mixture comprising an aqueous solution of isoprene, a hypochlorite, and a stream of gaseous carbon dioxide;
   (b) isolating 1-chloro-2-methyl-3-buten-2-ol as a reaction product from said first reaction mixture; and
   (c) forming a second reaction mixture of 1-chloro-2-methyl-3-buten-2-ol, acetic acid, acetic anhydride and a strong acid catalyst;
   (d) isolating 4-chloro-3-methyl-2-buten-1-ol acetate as a reaction product from said second reaction mixture; and
   (e) forming a third reaction mixture of 4-chloro-3-methyl-2-buten-1-ol acetate, dimethyl sulfoxide, and a non-nucleophilic base selected from the group consisting of dibasic sodium phosphate and dibasic potassium phosphate;
   (f) isolating E-4-acetoxy-2-methyl-2-butenal as a reaction product from said third reaction mixture.

9. The process of claim 8 further including in said third reaction mixture a bromide salt.

10. The process of claim 9 further including in said third reaction mixture a phosphate buffer.

* * * * *